United States Patent [19]

Malen et al.

[11] Patent Number: 4,496,557
[45] Date of Patent: Jan. 29, 1985

[54] TRICYCLIC ETHERS, THEIR PREPARATION AND THE PHARMACEUTICAL COMPOSITIONS CONTAINING THEM

[75] Inventors: Charles Malen, Fresnes; Jean-Claude Poignant, Bures s/Yvette, both of France

[73] Assignee: Adir, Neuilly-sur-Seine, France

[21] Appl. No.: 408,451

[22] Filed: Aug. 16, 1982

[30] Foreign Application Priority Data

Aug. 27, 1981 [FR] France .............................. 81 16347

[51] Int. Cl.$^3$ .................. A61K 31/33; A61K 31/335; C07D 313/12; C07D 267/18
[52] U.S. Cl. .................................... 514/211; 549/354; 549/390; 549/391; 548/518; 548/525; 546/196; 546/198; 544/375; 514/253; 514/320; 514/422; 514/450; 260/330.6
[58] Field of Search ...................... 549/390, 391, 354; 260/330.6; 424/278, 244, 283, 250, 267, 274; 544/375; 546/198, 196; 548/518, 525

[56] References Cited

U.S. PATENT DOCUMENTS 3,524,855 8/1970 Schindler et al. .................... 549/354
3,609,167 9/1971 Zirkle ..................................... 549/354

OTHER PUBLICATIONS

Melloni et al., Chem. Abstracts, 97, 162823a (1982), (Abstract of French Patent 2,492,378).

Primary Examiner—Nicky Chan
Attorney, Agent, or Firm—Gordon W. Hueschen

[57] ABSTRACT

Compounds corresponding to the general formula:

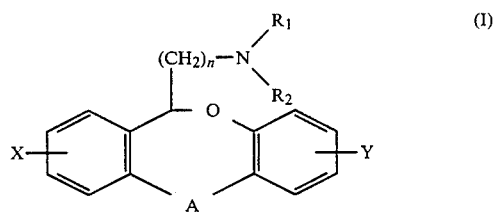

in which

X and Y identical or different, represent a hydrogen or a halogen atom, a lower alkyl, a lower alkoxy or a trifluormethyl group, A represents a methylene group, a direct bond or an imino—NR$_3$— group in which R$_3$ is a hydrogen atom or a lower alkyl or lower alkanoyl group R$_1$ and R$_2$ identical or different, each represents a hydrogen atom or a lower alkyl group, or together with the nitrogen atom to which they are attached they form a pyrrolidino, piperidino or methyl-4 piperazine group, and n represents an integer from 1 to 3, in their racemic or optical isomeric forms, as well as their salts of addition with a therapeutically compatible mineral or organic acid.

These compounds are useful as antidepressants.

13 Claims, No Drawings

TRICYCLIC ETHERS, THEIR PREPARATION AND THE PHARMACEUTICAL COMPOSITIONS CONTAINING THEM

The subject of the present invention is new tricyclic ethers carrying an amino-alkyl chain, their preparation and the pharmaceutical compositions containing them.

Specifically, the invention is concerned with compounds corresponding to the general formula:

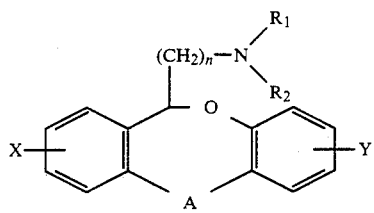

in which:

X and Y, identical or different, each represents a hydrogen or halogen atom, lower alkyl, lower alkoxy or trifluoromethyl group.

A represents a methylene group, an imino group —$NR_3$— (in which $R_3$ is a hydrogen atom, lower alkyl or lower alkanoyl group) or a direct bond.

$R_1$ and $R_2$, identical or different, each represents a hydrogen atom or a lower alkyl group, or, with the nitrogen atom to which they are attached, together form a pyrrolidine, piperidino or 4-methyl piperazino group, and n represents a whole number from 1 to 3, inclusive, n being 2 when $NR_1R_2$ is a heterocyclic radical.

By lower alkyl, alkoxy or alkanoyl group is understood groups having from 1 to 4 carbon atoms.

The invention is concerned also with salts of addition of the compounds with the general formula I with mineral or organic therapeutically compatible acids.

The compounds with general formula I have an asymmetric carbon atom and for this reason can be dissolved into their optical isomers. The isomers form part of the invention equally with the racemic compounds.

In order to facilitate the identification of the compounds of the examples appearing in the table, the following sub-families of compounds can be distinguished.

(a) the 6,11-dihydro-dibenzo (b,e) oxepines: (formula I: A=methylene)

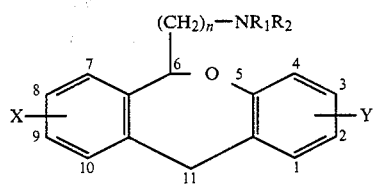

(b) the 5,11-dihydro dibenzo (b,e) 1,4-oxazepines: (formula I: A=$NR_3$)

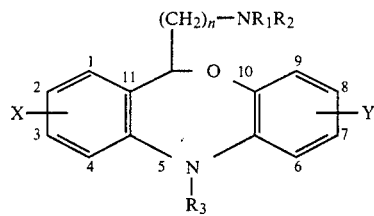

(c) the 6H-dibenzo (b,d) pyrans: (formula I, A=connection)

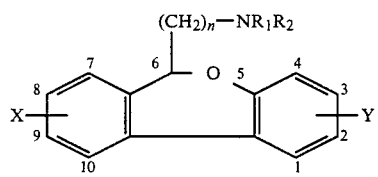

Among the acids which can be added to compounds with the general formula I in order to form a salt of addition there can be cited for example hydrochloric acid, phosphoric acid, tartaric acid citric acid, fumaric acid, maleic acid, oxalic acid, etc.

The invention also has as its subject a process of preparation for the compounds with the general formula I which process is characterised in that:

(a) a lactone with the general formula III of the plate of formulae, in which the significance of the substituents X Y and A is the same as in the formula I is submitted to the selective action of a ylid of alkoxycarbonyl-methyl phosphonium with the formula (IV)

$$Ar_3P^+—CH^-—COOR_4 \quad (IV)$$

in which Ar represents a phenyl or a substituted phenyl radical and $R_4$ is a lower alkyl or aralkyl radical substituted or not substituted, so as to form the (alkoxycarbonyl) methylidene derivative corresponding to the general formula (V) in which the substituents A, X, Y and $R_4$ retain the significances supplied above, (b) the latter is submitted to the action of a hydrogenation agent so as to form an (alkoxy carbonyl) methylene derivative with the general formula VI in which the substituents X, Y,$R_4$ and A have the same definition as above, then (c) *either* the latter is reduced by the action of a hydrogenation agent, in particular by a mixed hydride of alkali metal so as to obtain an alcohol with a general formula (VII) on plate I in which X, Y and A are defined as previously, (d) this alcohol is converted by means of a hydrohalic acid or sulphonic acid into a halide or suphonate corresponding to formula VIII on plate I in which the definition of the substituents X, Y and A remain unchanged and Z is Cl, Br, I, alkyl —$SO_3$ or aryl $SO_3$ (in particular p-toluenesulphonate), then (e) *either* the latter is made to react with an amine with the general formula (IX) (see plate 2)

$$HN\begin{matrix}R_1\\ \\R_2\end{matrix} \qquad (IX)$$

in which $R_1$ and $R_2$ have the same definition as in formula I and obtain an ethylamine derivative with the general formula (I) in which n=2, (f) *or* the compounds with the general formula (VIII) are submitted to the action of an alkaline cyanide or alkaline earth so as to form the nitrile with the general formula (X) in which X, Y and A remain the same and (g) this nitrile is reduced by a hydrogenation agent such as a mixed hydride or to a catalytic hydrogenation so as to form a amino propyl derivative with the general formula I in which n=3 and $R_1=R_2=H$, then, if desired, (h) an alkylising agent $R_1Z$ and/or $R_2Z$ in which $R_1$ and $R_2$ are lower alkyls and Z is a halogen or a sulphonyl group, so as to form the corresponding secondary or tertiary amine (formula (I): n=3, $R_1$ and/or $R_2$=lower alkyl).

(i) *or* in order to prepare the compounds with the formula (I) in which n=1, a compound with the formula VI obtained at stage (b) above, is made to react with hydrazine so as to obtain the corresponding hydrazide with the formula XI in which X, Y and A have the same significance as above (see plate 3), then (j) an alkaline nitrite is made to react on the latter in an acid medium so as to obtain the azide with formula XII in which X, Y and A retain the same significance as above, (k) the azide is heated in an aromatic solvent so as to obtain the corresponding isocyanate with the formula XIII (Curtius rearrangement) in which X, Y and A retain the same significance, then (l) *either* the isocyanate (XIII) is reduced by a metallic hydride so as to obtain a methylamine derivative with the general formula I in which n=1, $R_1=H$ and $R_2=CH_3$ (m) *or* phthalic anhydride is made to react on the isocyanate (XIII) so as to obtain the phthalimide corresponding, which is hydrolised into the primary amine with the formula (I) (n=1, $R_1=R_2=H$), then, if desired this is alkalised according to stage h) above.

The invention extends equally to a further process for obtaining the compounds of the general formula (I) in which n=2 characterised in that:

(n) a lactone of the general formula (III) in which X, Y and A are defined as in formula (I) is submitted to the action of a ylid of cyanomethyl-phosphonium with the general formula (IV′)

$$Ar_3P^+—CH^-—CN \qquad (IV')$$

in which Ar represents a phenyl radical possibly substituted so as to form a cyanomethylidene derivative with the general formula (XIV)
in which X, Y and A are defined as before (see plate 4)

(o) these derivatives are selectively hydrogenised into the corresponding amino ethylidene derivatives with the general formula (XV) in the Z or E form.
in which the substituents A, X and Y are as defined above, then (p) these latter are reduced by a hydrogenation agent such as a metallic hydride or by catalytic hydrogenation so as to form an ethylamine derivative with the formula (I) in which $R_1$ and $R_2=H$ and n=2 which if one wishes can be alkylised as previously (stage h) so as to obtain the corresponding compound in which $R_1$ and/or $R_2$ is a lower alkyl group.

A further subject of the invention is a process for obtaining the compounds with the general formula (I) in which n=2

(c) which process consists in submitting an alkoxycarbonylmethylidene compound with the general formula (V) to saponification carried out in an alkaline medium so as to form a (hydroxycarbonyl) methylidene derivative with general formula (XVI)

in which the substituents X, Y and A have the meanings already supplied in the Z or E form (see plate 5)

(r) which is condensed with an amine of the general formula (IX) previously defined in the presence of a carboxyl functionalising agent (cyanuryl chloride or carbodiimide) so as to form the corresponding methylidene amide with the general formula (XVI) in which the substituents $R_1$, $R_2$, X, Y and A have the previously supplied significances.

(s) which is reduced into an ethylamine derivative with the general formula (I) in which n=2.

The compounds with the general formula (I) obtained according to the processes described above can be resolved into their optically active isomers by a chiral acid. They can also be salified in a known manner by the addition of a mineral or organic acid.

The starting lactones with the formula III are generally described in the literature, nevertheless they can be obtained in a known manner for example starting with the corresponding benzoic acid with the general formula (II):

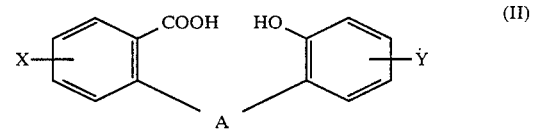

in which the substituents X,Y and A have same significances as in the formula (I), which is submitted to the action of a dehydrating agent such as acetic anhydride or to the action of thionyl chloride and to cyclisation by a tertiary amine so as to form the lactone (III).

The benzoic acids (II), as well as the various reagents of the formulae (IV), (IV′) and (IX) are known in the literature.

The following examples illustrates the invention. The plates of formulae attached explain the reactional scheme and the different structures of the compound produced. For the sake of simplicity, we shall not mention the degree of hydrogenation of the central heterocycle.

EXAMPLE 1 dl 6-(2-N-dimethylaminoethyl)-dibenzo (b,e) oxepine and its fumarate (a) 6-methoxycarbonyl-methylene-dibenzo (b,e) oxepine (general formula V:$R_4=CH_3$)

37.3 g (0.177 mole) of dibenzo (b,e) oxepin-6-one as described by W. BAKER and coll. (J.C.S. 1952, pp. 1452–57), 106.4 g of methoxycarbonylmethylene triphenylphosphoran and 375 ml of xylene are heated at reflux for 60 hours. The xylene is eliminated under vacuum. The residue is taken up by 250 cm³ of ether (ethyl oxide) to eliminate the triphenylphosphine oxide. The ether phase is taken to dryness. The residue (90 g) is shared in the following manner:

| | |
|---|---|
| dimethylformamide (DMF) | 765 ml |
| $H_2SO_4$ 3N | 765 ml, and |
| cyclohexane | 4 × 900 ml |

The cyclohexane phase is washed with water and dried, then evaporated to dryness. The residue (37.5 g) is crystallized from isopropyl ether. 5.7 g of the first isomer (M. Pt. 164°–168°) is recovered.

The evaporated mother liquors are filtered on silica and eluted with benzene. 22.1 g of the second isomer is recovered.

Total yield (Yt) (isomers Z+E)=59%.

NMR: 1st isomer: 1H ethylene signal at 5.9 ppm; 2nd isomer: 1H ethylene signal at 5.3 ppm.

The second isomer is also characterised by saponification in acid. (M. Pt. 190°–192°)

IR: CO 1720 cm⁻¹; OH 3100–2000 cm⁻¹.

NMR: 8H Ar (m) 7.1 ppm; 1H (s) 5.4 ppm; 2H (s) 4 ppm; $OCH_3$ absent.

(b) 6-methoxycarbonylmethyl-dibenzo (b,e) oxepine (General formula VI: $R_4=CH_3$)

2.7 g of the preceding ethylene ester (2nd isomer) is hydrogenated at ordinary temperature and pressure in 30 cm³ of acetic acid in the presence of 0.5 g of platinum oxide. The catalyst is filtered off and the solvent is evaporated under vacuum. After crystallization from hexane 1.2 g of product is obtained, M.Pt. 59°–63°.

(c) 6-(2-hydroxyethyl)-dibenzo (b,e) oxepine (General formula (VII)

6.8 g (0.025 mole) of the preceding saturated ester is reduced by 52 ml of a solution of lithium triethylborohydride in tetrahydrofuran THF (0.052 mole). After the usual treatment and distillation, there is isolated:

1.6 g B.P.$_{0.01}$=164°–168°; M. Pt. 80–81.

(d) tosylate of the preceding alcohol (formula VIII: Z=p-toluenesulphonyl)

2.4 g of the preceding alcohol is converted into tosylate by 2 g of p-toluene-sulphochloride in pyridine. 1.5 g of product is isolated M. Pt.=98°–102°.

(e) dl 6-(2-N-dimethylaminoethyl)-dibenzo (b,e) oxepine 3.3 g (0.0083 mole) of the preceding tosylate is heated in a sealed tube at 100° for 15 hours with 2.2 g of dimethylamine in 30 ml of acetonitrile. After acid-base treatment, 1.4 g of product is isolated which is then converted into acid fumarate in ethanol.

1.4 g is obtained, M. Pt. 105°–125° (with decomposition).

EXAMPLE 2 dl 11-(2-N-dimethylaminoethyl) 5-acetyl-dibenzo (b,e) 1,4-oxazepine and its hydrochloride Preparation of the starting product: 5-acetyl dibenzo (b,e) 1,4-oxazepin-(5H)one (general formula (III))

2.1 g (0.01 mole) of dibenzo (b,e) 1,4 oxazepin-(5H)one, prepared according to H. GURIEN and coll (J. Heter. Chem, 3 (4) 527, 1966) is taken to reflux for 2 hours with 8.5 cm³ of acetic anhydride. After evaporation of the volatile products under vacuum, the residue is recrystallized from 4 cm³ of ethyl acetate.

1.2 g is obtained, M. Pt. 124°–128°.

NMR: 3H singlet at 2.15 ppm, 8H (Ar) multiplet, 7.4–8 p.p.m.

IR: CO (lactone) 1730 cm⁻¹ (acetamide) 1670 cm⁻¹.

(a) 11-methoxycarbonylmethylene 5-acetyl-dibenzo (b,e) 1,4-oxazepine (forms Z and E) general formula V: $R_4=CH_3$ 30 g (0.12 mole) of the preceding acetyl derivative, 60.2 g (0.18 mole) of methoxycarbonylmethylene-triphenylphosphoran and 600 ml of anhydrous xylene are taken to reflux for 24 hours. The solvent is evaporated under vacuum. The crude residue is chromatographed on 2,400 g of silica 70–230 mesh (0.063 to 0.20 mm), with elution by a 50/50 mixture of cyclohexane and ethyl acetate.

30.6 g is obtained. Yt=76.2%; M.Pt. 108°–150°.

A sample of each of the two isomers is taken during the chromatography and recrystallized from acetonitrile (isomer Z) and ethyl acetate (isomer E)

NMR: Z IH (=CH) 5.9 ppm; M.Pt=152°–57°. E 1H (=CH) 5.5 ppm; M.Pt=160°–62°.

(b) dl 11-methoxycarbonylmethyl 5-acetyl dibenzo (b,e) 1,4 oxazepine (general formula VI $R_4=CH_3$)

20 g of the above mixture of Z+E isomers is hydrogenated under ordinary temperature and pressure in 200 ml of acetic acid in the presence of 500 mg of platinum oxide. After the theoretical quantity of hydrogen is absorbed, the catalyst is filtered off, the residue is taken up by ethyl ether, washed with 5% sodium bicarbonate, then taken to neutrality. The solvent is dried and evaporated. The residue is recrystallised from ethyl acetate.

11.6 g is obtained. M. Pt. 140°–144°. After recrystallization, M.Pt. 143°–145°.

IR: CO (ester) 1725 cm⁻¹, CO (amide) 1660 cm⁻¹.

NMR: 8H (Ar) (m) 6.7–7.5 ppm 1H (t) 6.1–6.4 ppm; 3H (s) 3.8 ppm; 2H (t) 3.4 ppm; 3H (s) 2.2 ppm.

(c) dl 11-(2-hydroxyethyl) 5-acetyl dibenzo (b,e) 1,4-oxazepine 17 g (0.054 mole of the above methyl ester in solution in 340 ml of anhydrous THF is treated with 108 ml of N lithium triethylborohydride (0.108 mole) in THF at ordinary temperature for 3 hours. The reactional mixture is hydrolysed with dilute aqueous HCl, then the solvent is evaporated under vacuum. After extraction with dichloromethane, washing with dilute sodium hydroxide then with water, by evaporation of the solvent 14 g of a glass is obtained which is constituted by the product concerned containing a very small quantity of de-acetylated alcohol (M. Pt. 107°–109°, isolatable by chromatography). The alcohol obtained could not be crystallized and the crude product is therefore used in the following stage.

NMR: 8H Ar (m) 7 ppm 1H 5.8 ppm; 2H 3.8 ppm; 1H exchangeable 2.5 ppm; 2H 2.2 ppm; 3H (s) 2 ppm.

(d) p-toluenesulphonate of the preceding alcohol 27.9 g (0.098 mole) of the crude alcohol above is converted into the paratoluenesulphonate ester by 19 g (0.1 mole) of paratoluene sulphochloride in pyridine. After the usual treatment, 30.8 g of a non-crystallizable product is obtained. Yt=72%

NMR: 12H Ar (m) 6.5–8 ppm; 1H 5.5–5.9 ppm; 2H 4.2–4.5 ppm; 6H 2.3 and 2.5 ppm; 2H 2–2.2 ppm.

(e) dl 11-(2-N-dimethylaminoethyl) 5-acetyl-dibenzo (b,e) 1,4-oxazepine 11 g (0.025 mole) of the crude product previously obtained is treated with 6.6 g of dimethylamine (0.15 mole) in 110 ml of acetonitrile in an autoclave at 100° for 15 hours. After isolation of the basic fraction, 6.7 g of an oil is obtained which is converted into the hydrochloride in anhydrous ether. 6 g of the hydrochloride is obtained which is re-cyrstallized from acetonitrile. M.Pt. 205°–225°. IR: CO(amide) 1675 cm$^{-1}$ NH+ 2400–2700 cm$^{-1}$.

EXAMPLE 3 dl 11-(2-N-dimethylaminoethyl)-dibenzo (b,e) 1,4-oxazepine and its hydrochloride 0.5 g of the compound prepared according to Example 2 in 1 cm$^3$ of methanol is treated with 0.5 ml of 20% NaOH, and taken to reflux for 20 hours. The solvent is then evaporated under vacuum and the residue extracted by ethyl ether is converted into the hydrochloride. 0.4 g of a product is obtained which is re-crystallised M.Pt. 208°–214°

NMR: 8H (Ar) 6.5–7.2 ppm; 1H exchangeable 6 ppm; 1H (t) 4.9–5.2 ppm; 10H (CH$_2$) (CH$_3$) 1.9–2.5 ppm.

EXAMPLE 4 dl 11-(2-N-dimethylamino-ethyl) 5-methyl dibenzo (b,e) 1,4-oxazepine and its fumarate 3.2 g (0.012 mole) of the compound obtained according to Example 3 in basic form is treated by 4.5 g (0.12 mole) of NaBH$_4$ in 42 ml of formic acid in an ice bath. After one night, this is diluted with water alkalised by ammonia. The product is extracted by dichloromethane, washed, then dried.

(NMR: N—CH$_3$ to 3.3 ppm) The base is converted into the acid fumarate and after re-crystallisation from ethanol, 2.5 g is obtained. M.Pt. 160°–175°.

Compounds Nos. 2 to 4 have been prepared according to example 1, compounds 6 and 7 according to example 2, and compound 10 according to example 4.

| COMPOUND | | X | Y | A | NR$_1$R$_2$ | n | MELTING (salt) |
|---|---|---|---|---|---|---|---|
| 1 | (EX 1) | H | H | —CH$_2$— | N(CH$_3$)$_2$ | 2 | 105–125° dec. (fumarate) |
| 2 | | H | H | —CH$_2$— | pyrrolidinyl | 2 | 154–158° (fumarate) |
| 3 | | H | H | —CH$_2$— | piperidinyl | 2 | 226–230° subl. (HCl) |
| 4 | | H | H | —CH$_2$— | 4-methylpiperazinyl | 2 | 215–225° dec. subl (2 HCl) |
| 5 | (EX 2) | H | H | —N(COCH$_3$)— | N(CH$_3$)$_2$ | 2 | 205–225° (HCl) |
| 6 | | H | H | —N(COCH$_3$)— | pyrrolidinyl | 2 | 220–230° (HCl) |
| 7 | | H | H | —N(COCH$_3$)— | piperidinyl | 2 | 245–260° (HCl) |
| 8 | (EX 3) | H | H | —NH— | N(CH$_3$)$_2$ | 2 | 208–214° (HCl) |
| 9 | (EX 4) | H | H | —N(CH$_3$)— | N(CH$_3$)$_2$ | 2 | 160–175° (fumarate) |
| 10 | | H | H | —N(C$_2$H$_5$)— | N(CH$_3$)$_2$ | 2 | 110–116° (fumarate) |

The compounds according to the invention have been submitted to a pharmacological study.

1—Inhibition of aggressiveness

This test was carried out on rats and mice which had previously undergone ablation of the olfactory bulbs and had been submitted to isolation according to the method described by L. Valzelli; Aggressive behaviour 1969, p 70-76 (Excerpa Medica Foundation-Amsterdam).

At doses of 10 mg/kg (mice) and 20 mg/kg (rats) by intraperitoneal route in solution in an aqueous solvent, the proportion of aggressive mice was reduced from 40 to 100% and the proportion of rats which killed others from 11 to 55%. The inhibiting effect on aggresiveness of the animals was not accompanied by any secondary effect such as hyperactivity or state of depression.

2—Antagonism to tetrabenazine

The compounds according to the invention injected in batches of 10 mice at doses of 10 mg/kg intraperitoneally inhibit by 30 to 100% the drooping of the eyelids caused by injection of tetrabenazine. The activity of the compound according to the invention in this test is often greater than that of mianserin taken as a reference product.

3—Antagonism to hypothermia

The compounds according to the invention injected by intraperitoneal or sub-cutaneous route at a dose of 10 mg/kg in mice antagonise hypothermia caused by the injection of 2.5 mg/kg of reserpine sub-cutaneously or of 15 mg/kg sub-cutaneously of apomorphine. In certain compounds this activity appears already at doses less than 1 mg/kg

4—Determination of the acute toxicity

The compounds according to the invention have been administered by the intraperitoneal route in solution in water at increasing doses going from 20 to 200 mg/kg to batches of 10 mice of Swiss strain weighing about 20 g. The animals are kept under observation for 8 days after which the number of deaths if there are any is ascertained.

The mean lethal dose LD 50 is calculated graphically according to the method of Tainter and Miller. It varies according to the compounds between 80 and 150 mg/kg by intraperitoneal route and from 250 to 350 mg/kg by oral route.

5—Neurological study

All the compounds of the invention have been administered to mice and rats by interperitoneal route at doses going from 5 mg/kg to the toxic dose (50—150 mg/kg) and have been the subject of a neurological study consisting in observing the behaviour the animals in a group according to the technique of Irwin. For a majority of the compounds no change in behaviour of the animals was noticed. Starting at doses of 25 to 50 mg/kg the motor function the tonus and the reflexes are noticeably reduced.

The compounds according to the invention are endowed with useful pharmacological properties. They are psychotropic substances which exhibit antidepressant and anxiolytic effects on the central nervous system. On animals they cause an inhibition of aggressiveness and have an anti hypothermic effect.

They can therefore be used in human or animal therapeutics as antidepressants and/or anxiolytic medicaments as well as in the treatment of near morbid states such as migraine. In children they are used for the treatment of difficulties at school associated with depression.

The invention also has as its subject the pharmaceutical compositions containing at least one compound with the general formula (I) or one of its salts of addition with an organic or mineral acid as active principle, in association or mixed with one or more excipients or inert non-toxic vehicles, pharmaceutically acceptable.

Among the pharmaceutical compositions according to the invention there can more particularily be cited those which are suitable for administration by parenteral, oral or rectal route and in particular tablets whether coated, non-coated or intended for delayed release, capsules, micro-capsules, pills, suspensions, drinkable solutions or emulsions, drops, injectable solutions or suspensions furnished in ampoules in multi-dose flasks or in auto-injectable syringes: suppositories.

Useful dosage varies according to the age and weight of the patient, the administration route and the nature of the therapeutic indication.

In a general way the unit dose ranges from 1 mg to 25 mg and the daily dosage from 5 to 100 mg for man. In veterinary medicine the dosage is adjusted according to the weight of the animal. In children the dosage will be considerably diminished as a function of the weight of the subject.

In addition certain compounds possess a useful activity against gastric secretions which appears on Shay's rat preparation at doses between 1 and 15 mg/kg by intraperitoneal route.

This property can be used in the pathology of gastroduodenal ulcers.

SYNTHESIS DIAGRAM

Plate 1

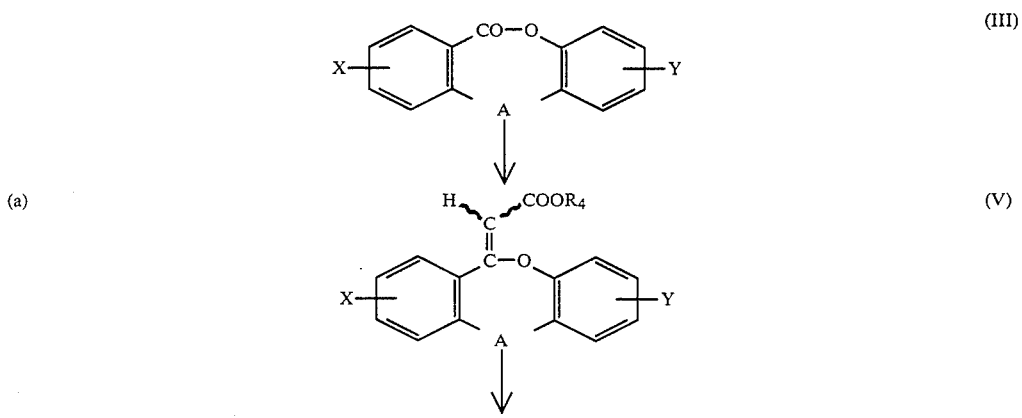

-continued
SYNTHESIS DIAGRAM
(b) 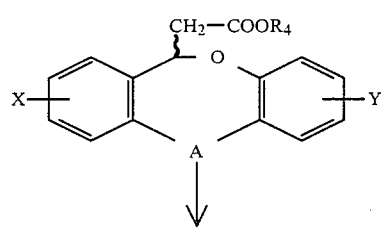 (VI)
(c) 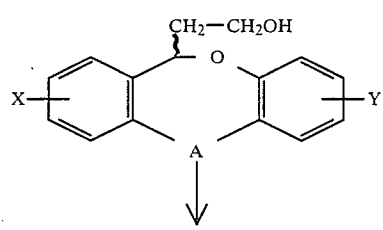 (VII)
(d) 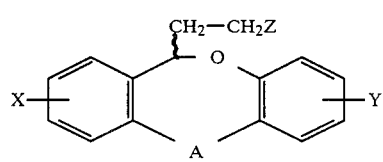 (VIII)
Plate 2
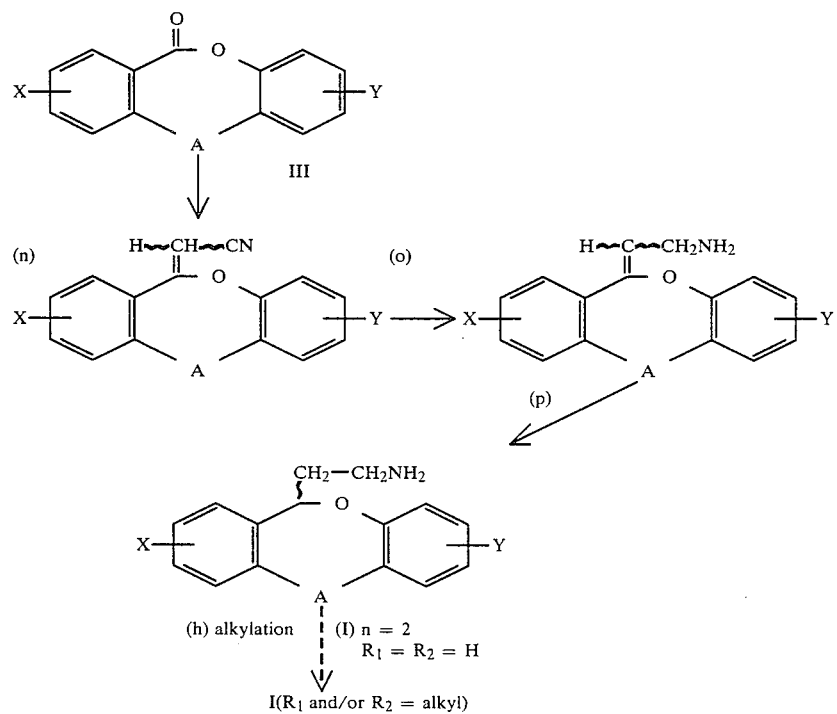
(h) alkylation ┆ (I) n = 2
                $R_1 = R_2 = H$
   ⇓
I($R_1$ and/or $R_2$ = alkyl)
Plate 3
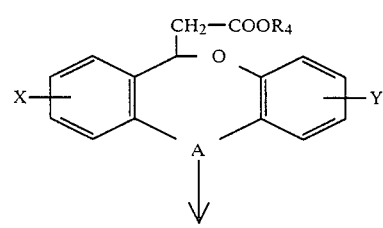 (VI)

-continued
SYNTHESIS DIAGRAM
(i) 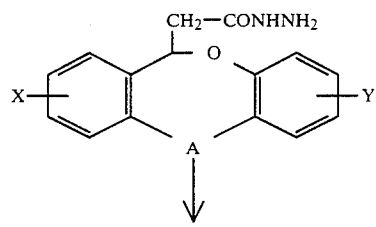 (XI)
(j) 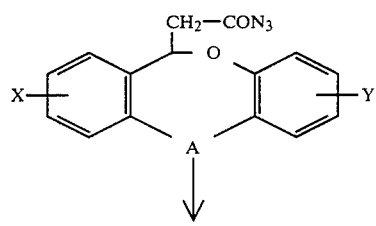 (XII)
(k) 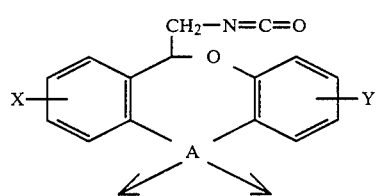 (XIII)
(l) 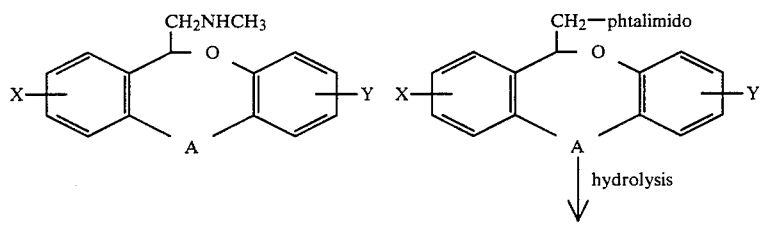
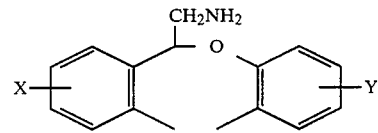
Plate 4
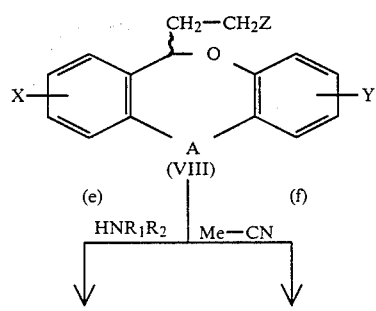

-continued
SYNTHESIS DIAGRAM
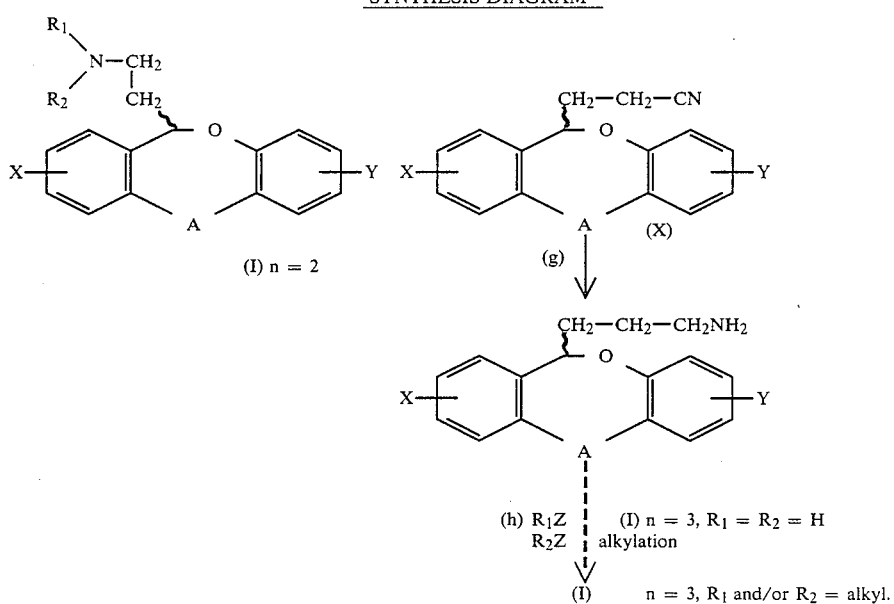
Plate 5
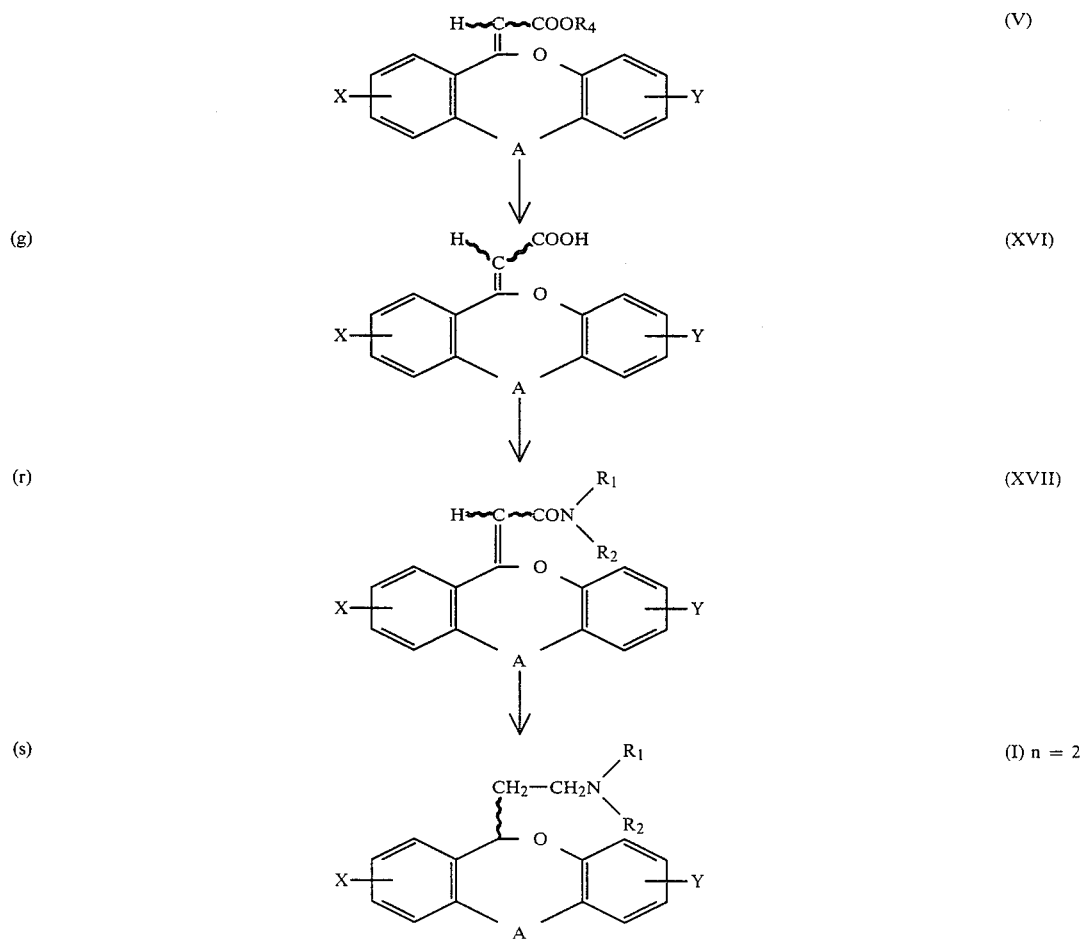
We claim:
1. A compound corresponding to the general formula:

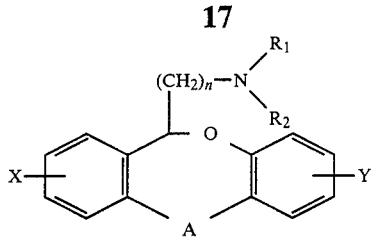 (I)

in which
- X and Y identical or different, represent a hydrogen or a halogen atom, a lower alkyl, a lower alkoxy or a trifluoromethyl group,
- A represents a methylene group or an —NR$_3$— group in which R$_3$ is a hydrogen atom or a lower alkyl or lower alkanoyl group
- R$_1$ and R$_2$ identical or different, each represents a hydrogen atom or a lower alkyl group, or together with the nitrogen atom to which they are attached they form a pyrrolidino, piperidino or 4-methylpiperazino group, and
- n represents an integer from 1 to 3, inclusive, n being 2 when NR$_1$R$_2$ is a heterocyclic radical, in their racemic or optical isomeric forms, as well as their salts of addition with a therapeutically compatible mineral or organic acid.

2. Compound according to claim 1 in which n=2.

3. Compound according to claim 1 in which A is a methylene group.

4. 6-(2-N-dimethylaminoethyl)-dibenzo (b,e) oxepine fumarate.

5. 11-(2-N-dimethylaminoethyl)-5-methyl-dibenzo (b,e)-1,4-oxazepine fumarate.

6. A pharmaceutical composition useful in treating depression containing as active principle an antidepressive amount of at least one compound according to any one of claims 1 to 5 in association with or mixed with a non-toxic pharmaceutically-acceptable excipient or inert vehicle.

7. A pharmaceutical composition according to claim 6 in which the excipient or the vehicle is one suitable for use by parenteral or by oral route.

8. Method for treating depression in a patient which comprises administering to said patient a therapeutically-effective dose of a compound according to claim 1.

9. Compound of claim 1 which is 6-(2-N-dimethylaminoethyl)-dibenzo (b,e) oxepine or a pharmaceutically-acceptable acid addition salt thereof.

10. Compound of claim 1 which is 11-(2-n-dimethylaminoethyl)-5-methyl-dibenzo (b,e)-1,4-oxazepine or a pharmaceutically-acceptable acid addition salt thereof.

11. Compound according to claim 1 in which A is —NR$_3$—, wherein R$_3$ has the meaning assigned thereto in claim 1.

12. Compound of claim 1 which is 11-(2-N-dimethylaminoethyl)-5-acetyl-dibenzo(b,e)-1,4-oxazepine or a pharmaceutically-acceptable acid addition salt thereof.

13. Compound of claim 1 which is 11-(2-N-dimethylaminoethyl)-dibenzo(b,e)-1,4-oxazepine or a pharmaceutically-acceptable acid addition salt thereof.

* * * * *

UNITED STATES PATENT AND TRADEMARK OFFICE
CERTIFICATE OF CORRECTION

PATENT NO. : 4,496,557
DATED : January 29, 1985
INVENTOR(S) : Charles Malen and Jean-Claude Poignant It is certified that error appears in the above-identified patent and that said Letters Patent is hereby corrected as shown below:

Col. 1, line 35; "pyrrolidine," should read -- pyrrolidino, --

Col. 4, line 9; " (c) " should read -- (q) --

Cols. 13 & 14, the fourth diagram from the top, it has two diagrams and the first one is labeled "(l)" and the second one should be labeled -- (m) --

Col. 18, line 18; " -n- " should read -- -N- --

Signed and Sealed this

Fifth Day of November 1985

[SEAL]

Attest:

DONALD J. QUIGG

Attesting Officer

Commissioner of Patents and Trademarks